(12) United States Patent
Van Dyke

(10) Patent No.: US 7,001,987 B2
(45) Date of Patent: Feb. 21, 2006

(54) HYDROGEL WITH CONTROLLABLE MECHANICAL, CHEMICAL, AND BIOLOGICAL PROPERTIES AND METHOD FOR MAKING SAME

(75) Inventor: Mark E. Van Dyke, Fair Oaks Ranch, TX (US)

(73) Assignee: Keraplast Technologies, Ltd., San Antonio, TX (US)

( * ) Notice: Subject to any disclaimer, the term of this patent is extended or adjusted under 35 U.S.C. 154(b) by 247 days.

(21) Appl. No.: 10/127,523

(22) Filed: Apr. 22, 2002

(65) Prior Publication Data

US 2003/0224052 A1 Dec. 4, 2003

(51) Int. Cl.
C07K 14/435 (2006.01)

(52) U.S. Cl. .................. 530/357; 514/12; 530/350; 530/356; 530/402; 530/409; 530/410; 530/842

(58) Field of Classification Search ............... 514/12; 530/350, 356, 357, 402, 409, 410, 842
See application file for complete search history.

(56) References Cited

U.S. PATENT DOCUMENTS

| | | | |
|---|---|---|---|
| 922,692 A | 5/1909 | Goldsmith | |
| 926,999 A | 7/1909 | Neuberg | |
| 960,914 A | 6/1910 | Heinemann | |
| 2,434,688 A | 1/1948 | Evans | |
| 3,250,682 A | 5/1966 | Wilmsmann et al. | |
| 3,642,498 A | 2/1972 | Anker | |
| 3,677,693 A | 7/1972 | Fillingham | |
| 3,842,848 A | 10/1974 | Kajala ........................ | 132/7 |
| 4,041,150 A | 8/1977 | Karjala ........................ | 424/71 |
| 4,279,996 A | 7/1981 | Yoshioka et al. .......... | 435/69.1 |
| 4,423,032 A | 12/1983 | Abe | |
| 4,474,694 A | 10/1984 | Coco | |
| 4,495,173 A | 1/1985 | Matsunaga et al. | |
| 4,504,644 A | 3/1985 | Lang et al. | |
| 4,570,629 A | 2/1986 | Widra | |
| 4,659,566 A | 4/1987 | Petrow ........................ | 424/71 |
| 4,751,074 A | 6/1988 | Matsunaga | |
| 4,895,722 A | 1/1990 | Abe | |
| 4,906,460 A | 3/1990 | Kim et al. ................... | 424/70 |
| 4,959,213 A | 9/1990 | Brod et al. .................. | 514/21 |
| 5,047,249 A | 9/1991 | Rothman | |
| 5,073,294 A | 12/1991 | Shannon et al. | |
| 5,202,053 A | 4/1993 | Shannon | |
| 5,219,562 A | 6/1993 | Fujiu et al. .................. | 424/71 |
| 5,258,501 A | 11/1993 | Barbaric et al. | |
| 5,276,138 A | 1/1994 | Yamada et al. | |
| 5,288,489 A * | 2/1994 | Reich et al. ............... | 424/94.64 |
| 5,300,285 A | 4/1994 | Halloran et al. | |
| 5,356,433 A | 10/1994 | Rowland et al. | |
| 5,358,935 A | 10/1994 | Lankford et al. | |
| 5,412,076 A | 5/1995 | Gagnieu | |
| 5,424,062 A | 6/1995 | Schwan et al. ............. | 424/70.5 |
| 5,425,937 A | 6/1995 | Uchiwa et al. ............ | 424/70.14 |
| 5,444,154 A * | 8/1995 | O'Lenick, Jr. .............. | 530/356 |
| 5,505,952 A | 4/1996 | Jiang | |
| 5,520,925 A | 5/1996 | Maser | |
| 5,563,230 A | 10/1996 | Hsu et al. | |
| 5,654,471 A | 8/1997 | Zahn et al. | |
| 5,679,819 A | 10/1997 | Jones | |
| 5,712,252 A | 1/1998 | Smith | |
| 5,766,534 A * | 6/1998 | White et al. ............... | 264/258 |
| 5,833,880 A | 11/1998 | Siemensmeyer | |
| 5,932,552 A | 8/1999 | Blanchard et al. | |
| 5,942,009 A | 8/1999 | Burns ............................ | 8/432 |
| 5,948,432 A | 9/1999 | Timmons et al. .......... | 424/443 |
| 5,955,549 A | 9/1999 | Chang | |
| 5,989,461 A | 11/1999 | Coates et al. | |
| 6,087,462 A | 7/2000 | Bowers et al. | |
| 6,090,308 A | 7/2000 | Coates et al. | |
| 6,110,487 A | 8/2000 | Timmons et al. .......... | 424/443 |
| 6,124,265 A | 9/2000 | Timmons et al. ............ | 514/12 |
| 6,140,475 A * | 10/2000 | Margolin et al. ........... | 530/402 |
| 6,159,495 A | 12/2000 | Timmons et al. .......... | 424/443 |
| 6,159,496 A | 12/2000 | Blanchard | |
| 6,165,496 A | 12/2000 | Timmons et al. .......... | 424/443 |
| 6,211,296 B1 | 4/2001 | Frate et al. | |
| 6,270,791 B1 | 8/2001 | Van Dyke et al. .......... | 424/443 |
| 6,270,793 B1 | 8/2001 | Van Dyke et al. .......... | 424/443 |
| 6,274,155 B1 | 8/2001 | Van Dyke et al. .......... | 424/402 |
| 6,274,163 B1 | 8/2001 | Blanchard et al. .......... | 424/443 |

(Continued)

FOREIGN PATENT DOCUMENTS

| | | |
|---|---|---|
| EP | 0097907 | 1/1984 |
| EP | 0 298 684 A3 | 1/1989 |
| EP | 0 468 797 A2 | 1/1992 |
| EP | 0540357 | 5/1993 |
| FR | 0454 600 A1 | 10/1991 |
| JP | 4-189833 | 7/1992 |
| JP | 2002-113815 | 4/2002 |
| WO | WO 93/10827 | 6/1993 |
| WO | WO 93/22397 | 11/1993 |
| WO | WO 98/08550 | 3/1998 |
| WO | WO 9931167 | 6/1999 |
| WO | WO 03008006 | 1/2003 |

OTHER PUBLICATIONS

Nagase Chemtex product information on Denacols, 2001.*
J.M. Gillespie, et al., "Amino Acid composition of a Sulphur–Rich Protein from Wool," BIOCHIM. BIOPHY. ACTA, (1960) pp. 538–539; vol. 39.
Keith H. Gough, et al., "Amino Acid Sequences of alpha Helical Segments from S–Carboxymethylkerateine–A: Complete Sequence of a Type–I Segment," BIOCHEM. J. (1978), pp. 373–385; vol. 173.
Thomas C. Elleman, et al., "Amino Acid Sequences of alpha Helical Segments from S–Carboxymethylkerateine–A: Statistical Analysis," BIOCHEM. J. (1978), pp. 387–391, vol. 173.

(Continued)

Primary Examiner—Robert A. Wax
(74) Attorney, Agent, or Firm—Vinson & Elkins L.L.P.

(57) ABSTRACT

Networks, hydrogels, and methods for networks and hydrogels comprising proteinaceous material consisting essentially of water soluble proteins and covalent interprotein crosslinks other than disulfide crosslinks.

5 Claims, 4 Drawing Sheets

U.S. PATENT DOCUMENTS

| | | | |
|---|---|---|---|
| 6,280,474 B1 * | 8/2001 | Cassidy et al. | 623/16.11 |
| 6,303,150 B1 * | 10/2001 | Perrier et al. | 424/491 |
| 6,316,598 B1 | 11/2001 | Van Dyke et al. | |
| 6,352,699 B1 | 3/2002 | Mondet et al. | |
| 6,361,767 B1 | 3/2002 | Malle et al. | |
| 6,371,984 B1 | 4/2002 | Van Dyke et al. | |
| 6,379,690 B1 | 4/2002 | Blanchard et al. | |
| 6,399,051 B1 | 6/2002 | Dannecker et al. | |
| 6,432,435 B1 | 8/2002 | Timmons et al. | |
| 6,435,193 B1 | 8/2002 | Cannell et al. | |
| 6,461,628 B1 | 10/2002 | Blanchard et al. | |
| 6,565,842 B1 * | 5/2003 | Sojomihardjo et al. | 424/85.1 |

OTHER PUBLICATIONS

David McC. Hogg, et al., "Amino Acid Sequences of alpha–Helical Segments from S–Carboxymethlk-erateine–A:. Tryptic and Chymotryptic Peptides from a Type–II Segment," BIOCHEM. J. (1978), pp. 353–363; vol. 173.

W. Gordon Crewther, et al., "Amino Acid Sequences of alpha –Helical Segments from S–Carboxymethylk-erateine–A: Complete Sequence of a Type–II Segment," BIOCHEM. J. (1978), pp. 365–371; vol. 173.

C. Earland, et al., "Studies on the Structure of Keratin: II, The Amino Acid Context of Fractions Isolated from Oxidized Wool," BIOCHEMICA ET BIOPHYSICA ACTA (1956), pp. 405–411, vol. 22.

J.M. Gillespie, et al., "Preparation of an Electrophoretically Homogeneous Keratin Derivative from Wool," Short Communications, Preliminary Notes, (1953), pp. 481–482, vol. 12.

Maurice J. Frenkel, et al., "The Isolation and Properties of a Tyrosine–Rich Protein from Wool: Component 0.62," EUR. J. BIOCHEM, (1973) pp. 112–119, vol. 34.

R.J. Blagrove, et al., "The Electrophoresis of the High–Tyrosine Proteins of Keratins on Cellulose Acetate Strips," Comp. Biochem. Physiol., (1975) pp. 571–572, vol. 50B.

Robert C. Marshall, et al., "Successful Isoelectric Focusing of Wool Low–Sulphur Proteins," Journal of Chromatography, (1979) pp. 351–356, vol. 172.

Robert C. Marshall, "Chracterization of the Proteins of Human Hair and Nail by Electrophoresis," The Journal of Investigation Dermatology, (1983) pp. 519–524, vol. 80.

W. G. Crewther, et al. "Helix–Rich Fraction from the Low–Sulphur Proteins of Wool," Nature, (Jul. 17, 1965) p. 295, No. 4994.

H. Lindley, et al., "Occurrence of the Cys–Cys Sequence in Keratins," J. Mol. Biol., (1967) pp. 63–67, vol. 30.

Robert C. Marshall, "Genetic Variation in the Proteins of Human Nail," The Journal of Investigative Dermatology, (1980) pp. 264–269, vol. 75.

M. E. Campbell, et al., "Compositional Studies of High–and Low–Crimp Wools," Aust. J. Biol. Sci., (1972) pp. 977–987, vol. 25.

P.J Reis, et al. "A Relationship between Sulphur Content of Wool and Wool Production by Merino Sheep," Aust. J. Biol. Sci., (1967) pp. 153–163, vol. 20.

Robert C. Marshall, et al., "The Keratin Proteins of Wool, Horn and Hoof from Sheep," Aust. J. Biol. Sci, (1977) pp. 389–400, vol. 30.

J.M. Gillespie. "Reaction of Sodium Borohydride with Wool," Nature, (Jan. 31, 1959) pp. 322–323, vol. 183.

David R. Goddard, et al., "A Study on Keratin," J. Bio. Chem., (1934) pp. 605–614, vol. 106.

L.M. Dowling, et al., "Isolation of Components from the Low–Sulphur Proteins of Wool by Fractional Preciptation Preparative Biochemistry," (1974) pp. 203–226, vol. 4 (3).

W.G. Crewther, et al., "Reduction of S–Carboxymethylcysteine and Methionine with Sodium in Liquid Ammonia," Biochim. Biophys. Acta, (1969) pp. 609–611, vol. 164.

W.T. Agar, et al., "The Isolation from Wool of a Readily Extractable Protein of Low Sulphur Content," Biochim. Biophys Acta, (1958) pp. 225–226, vol. 27.

H. Lindley, et al., "The Reactivity of the Disulphide Bonds of Wool," Biochem J. (1974) pp. 515–523; vol. 139.

M. Schoring, et al., "Synthesis of Nerve Growth Fractor mRNA in Cultures of Developing Mouse Whisker Pad, A Peripheral Target Tissue of Sensory Trigeminal Neurons," The Journal of Cell Biology, (Mar. 1993) pp. 1471–1479, vol. 120, No. 6.

S. Mitsui, et al., "Genes for a Range of Growth Factors and Cyclin–Dependent Kinase Inhibitors are Expressed by Isolated Human Hair Follicles," British Journal of Dermatology (1997) pp. 693–698, vol. 137.

B.K. Filshie, et al., "The Fine Structure of alpha –Keratin," J. Mol. Biol. (1961) pp. 784–786, vol. 3.

R.D.B. Fraser, et al., "Structure of alpha –Keratin," Nature, (Feb. 28, 1959) pp. 592–594, vol. 183.

R.D.B. Fraser, et al. "Helical Models of Feather Keratin Structure," Nature, (Sep. 22, 1962) pp. 1167–1168, vol. 195.

B.K.Filshie, et al., "An Electron Microscope Study of the fine Structure of Feather Keratin," The Journal of Cell Biology (1962) pp. 1–12, vol. 13.

W.G. Crewther, et al., "Low–Sulfur Proteins from alpha Keratins. Interrelationships between their Amino Acid Compositions, alpha–Helix Contents, and the Supercontraction of the Parent Keratin," BIOPOLYMERS (1966) pp. 905–916, vol. 4.

G.M. Bhatnagar, et al., "The Conformation of the High–Sulphur Proteins of Wool 1. The Preparation and Properties of a Water–Sulphur Metakeratin," Int. J. Protein Research I. (1969), pp. 199–212.

W.G. Crewther, et al., "The Preparation and Properties of a Helix–Rich Fraction Obtained by Partial Proteolysis of Low Sulphur S–Carboxymethlkerateine from Wool," (1967) The Journal of Biological Chemistry (Issue of Oct. 10), pp. 4310–4319, vol. 242, No. 19.

D.A.D. Parry, et al., "Structure of alpha –Keratin: Structural Implication of the Amino Acid Sequences of the Type I and II Chain Segments," J. Mol. Biol. (1977) pp. 449–454, vol. 113.

E. Suzuki, et al., "X–Ray Diffraction and Infrared Studies of an alpha –Helical Fragment from alpha –Keratin," J. MolL. Biol. (1973) pp. 275–278, vol. 73.

G.M. Bhatnagar, et al., "The Conformation of the High–Sulphur Proteins of Wool: II. Differerence Spectra of Kerateine–B," Int. J. Research1; (1969) pp. 213–219.

Dean R. Hewish, et al., "In Vitro Growth and Differentiation of Epithelial Cells Derived from Post–Embroyonic Hair Follicles," Aust. J. Biol. Sci., (1982) pp. 103–109, vol. 35.

A.M. Downes, et al., "A Study of the Proteins of the Wool Follicle," Aust. J. Biol. Sci., (1966) pp. 319–333, vol. 19.

G. E. Rogers, et al., "Keratin Protofilaments and Riobsomes from Hair Follicles," Nature, (Jan. 2, 1965), pp. 77–78, vol. 205.

P.M. Steinert, et al., "In Vitro Studies on the Synthesis of Guinea Pig Hair Keratin Proteins," Biochimica et Biophysica Acta, (1973) pp. 403–412, vol. 312.

G.E. Rogers, et al., "Some Observations on the Proteins of the Inner Root Sheath Cells of Hair Follices," Biochimica et Biophysica Acta, (1958) pp. 33–43, vol. 29.

Leslie N. Jones, et al., "Studies of Developing Human Hair Shaft Cells in Vitro," The Journal of Investigative Dermatology., (Jan. 1988) pp. 58–64, vol. 90.

Trevor Jarman, et al., "Prospects for Novel Biomaterials Development," Online Publications, Pinner, Uk, Presented at Biotech '85 (Europe) (1985) pp. 505–512.

Akira Tachibana, et al., "Fabrication of Wool Keratins Sponge Scaffolds for Long–Term Cells Cultivation," Journal of Biotechnology, (2002) pp. 165–170, vol. 93.

J.M. Gillispie, et al., "Periodicity in High–sulphur Proteins from Wool," Nature, (Sep. 18, 1965) pp. 530–531, vol. 246.

Kiyoshi Yamauchi, "The Development of Keratin: Characteristics of Polymer Films," [Research Report]; pp. 1–12.

"Scattering to Structural Foams, Skin, Synthetic" Encyclopedia of Polymer and Science and Engineering, (1989) pp. 335–345, vol. 15.

J.M Gillespie, et al., "Proteins Rich in Glycine and Tyrosine from Keratins," Comp. Biochem. Physiol., (1972) pp. 723–734, vol. 41B.

R.D.B. Fraser, et al., "Tyrosine–Rich Proteins in Keratins," Comp. Biochem. Physiol., (1973) pp. 943–947, vol. 44B.

J.M. Gillespie, et al., "Relation Between the Tyrosine Content of Various Wools and their Content of a Class of Proteins Rich in Tyrosine and Glycine," Aust. J. Biol. Sci., (1971) pp. 1189–1197, vol. 24.

J.M. Gillespie, et al., "The Macroheterogeneity of Type I Tyrosine–rich Proteins of Merino Wool," Aust. J. Biol. Sci., (1974) pp. 617–627, vol. 27.

E.G. Bendit, et al., "The Probable Role and Location of High–Glycine–Tyrosine Proteins in the Structure of Keratins," BIOPOLYMERS, (1978) pp. 2743–2745, vol. 17.

Robert C. Marshall, et al. "High–sulphur Proteins from alpha –Keratins: 11.* Isolation and Partial Characterization of Purified Components from Mouse Hair," Aust. J. Biol. Sci. (1976) pp. 11–20, vol. 29.

Robert C. Marshall, et al. "High–Sulphur Proteins from alpha –Keratins: 1. Heterogeneity of the Proteins from Mouse Hair," Aust. J. Biol. Sci. (1976) pp. 1–10, vol. 29.

R. L. Darskus, et al. "The Possibility of Common Amino Acid Sequences in High–Sulphur Protein Fractions From Wool," Aust. J. Biol. Sci. (1969) pp. 1197–1204, vol. 22.

Robert C. Marshall, et al. "Heterogeneity and Incomplete Disulfide Reduction in the High–Sulfur Proteins of Wool," Aust. J. Biol. Sci. (1978) pp. 219–229, vol. 31.

H. Lindley, et al., "The Preparation and Properties of a Group of Proteins from the High– Sulphur Fraction of Wool," Biochem. J. (1972) pp. 859–867, vol. 128.

J.M. Gillespie, et al., "Evidence of Homology in a High-Sulphur Protein Fraction (SCMK–B2) of Wool and Hair alpha –Keratins," Biochem. J. (1968) pp. 193–198, vol. 110.

J.M. Gillespie, et al., "A Comparative Study of High–Sulphur Proteins from alpha–Keratins," Comp. Biochem. Physiol. (1965) pp. 175–185, vol. 15.

J.M. Gillespie, et al., "High–Sulphur Proteins as a Major Cause of Variation in Sulphur Content Between alpha –Keratins," Nature (Sep. 18, 1965) pp. 1293–1294, vol. 207.

R.D.B. Fraser, et al., "Molecular Organization in Alpha–Keratin," Nature, (Mar. 17, 1962) pp. 1052–1055, vol. 193.

Dr. P. Alexander, et al., "Structure of Wool Fibres," Nature, (Sep. 2, 1950) pp. 396–398.

Node, et al., "Hard Acid and Soft Nucleophile System. 2. Demethylation of Methyl Ethers of Alcohol and Phenol with an Aluminum Halide–Thiol System," J. Org. Chem (1980), pp. 4275–4277. vol. 45.

Ito, et al., "Biocompatibility of Denatured Wool Keratin," Konbushi Ronbunshu [Collected Essays on Polymers], (Apr. 1982) pp. 249–256, vol. 39, No. 4.

Tatsuya and Ishii, "Keratin Protein High Pressure Molded Article,"; Japanese Patent Application, (Dec. 3, 1993), total of six pages, Public Patent Announcement 1993–320358.

Saeki, Yokogawa, and Uehara, "Production Method For Water–soluble Keratin Protein," Japanese Patent Application, (Feb. 21, 1990), total of five pages, Public Patent Announcement 1990–51533.

Miyamoto and Tsushima, "A Method for Preparing a Keratin Substance with a Low Molecular Weight," Japanese Patent Application, (Jul. 8, 1982), total of five pages; Public Patent Disclosure Bulletin S57–109797.

R.D.B. Fraser, "The Chain Configuration of Wool Keratin," Short Communications, Preliminary Notes, (1953) pp. 482–483, vol. 12.

R.D.B. Fraser, et al., "Microscopic Observations of the Alkaline–Thioglycollate Extraction of Wool," Short Communications, Preliminary Notes, (1953) pp. 484, vol. 12.

Weetall HH.; Preparation of immobilized proteins covalently coupled through silane coupling agents to inorganic supports; Applied Biochemistry and Biotechnology; 1993; 157–188; 41(3).

Weetall, HH.; Preparation of immobilized proteins covalently coupled through silane coupling agents to inorganic supports; Advances in Molecular and Cell Biology; 1996; 161–192; 15A.

Van Dyke Mark et al., Development of keratin coatings for osteoinduction on titanium, ,Abstracts of Papers American Chemical Society, vol. 224, No. 1–2, 2002,Aug. 18–22, 2002.

Tanaka, Yoshio et al., Reaction of Wool Keratin with Epoxides, Proceedings International Wolltexil–Forschungskonf, vol. 3, 1976, pp. 192–201.

Fraenkel–Conrat, H., The Action of 1, 2–Epoxides on Proteins, Journal of Biological Chemistry, vol. 154, No. 1, Jun. 1, 1944.

S. F. Sadova and A. A. Konkin. Grafting of vinyl monomers onto wool keratin in an oxidation–reduction system. Zh Vses Khim O–va 1967; 12(5):596–7.

Iwata, et al.; Coating Film For Living Tissues; Nov. 2, 1985; total of 9 pages; Japanese Patent Application Kokai Publication No. Sho 60–220068.

Endo; De–Allergenized Rubber or Plastic Molding Used in the Field of Medical Care; Apr. 16, 2002; total of 5 pages; Japanese Patent Application Kokai Publication No. 2002–113815.

Yoshioka et al; Modified Animal Hair or Wool Powder; Jul. 11, 1989; total of 13 pages; Japanese Unexamined Patent Application Publication H01–174528.

Miyamoto et al; Process for Producing Modified Keratin Protein; Feb. 6, 1982; total of 4 pages; Japanese Patent Application Kokai Publication No. Sho 57–23631.

Yamauchi et al; Keratin Microcapsule, Production of Keratin Microcapsule, and Cosmetics Containing Keratin Microcapsules; Dec. 22, 1998; total of 5 pages; Japanese Patent Application Kokai Publication No. H10–337466.

* cited by examiner

HYDROGEL WITH CONTROLLABLE MECHANICAL, CHEMICAL, AND BIOLOGICAL PROPERTIES AND METHOD FOR MAKING SAME

CROSS-REFERENCE TO RELATED APPLICATIONS

The present application is related to the following pending applications: U.S. patent application Ser. No. 10/133,885, filed Apr. 26, 2002, which is a continuation-in-part of copending U.S. patent application Ser. No. 10/119,477, filed Apr. 10, 2002. The present application is also related to the following provisional applications: U.S. Provisional Application 60/200,543, filed Apr. 27, 2000; U.S. Provisional Application 60/225,5 17, filed Aug. 15, 2000; U.S. Provisional Application 60/324,709, filed Sept. 25, 2001; U.S. Provisional Application 60/393,958, filed Jul. 5, 2002; and U.S. Provisional Application 60/399,039, filed Jul. 25, 2002.

FIELD OF THE APPLICATION

The present application relates to proteinaceous hydrogels, preferably keratinaceous hydrogels, that afford broad control over mechanical, chemical, and biological properties of the hydrogel. The application also relates to methods for producing the proteinaceous hydrogels

BACKGROUND OF THE INVENTION

Proteins, particularly keratins, are beneficial in healing damaged epithelial tissues. Unfortunately, the chemical and engineering properties of proteins, such as keratins, have been relatively limited to those achieved using oxidative and reductive chemistries, and side chain protein/protein crosslinks. Water is inherently biocompatible. One strategy that has been effectively used to improve the biocompatibility of certain materials has been to infuse the material with a large amount of water. In some cases, synthetic materials that are only moderately tolerated by the human body have been rendered more biocompatible when formulated as low solids hydrogels. Certain proteins, such as keratin, are inherently biocompatible. Hydrogels made from biocompatible proteins have the advantage that they can have a relatively high solids content while retaining a high level of biocompatibility.

Previous keratin hydrogels either were particulate in nature and/or were crosslinked through cystine residues. Disulfide crosslinks are not hydrolyzable. As a result, the hydrogels were not readily biodegradable. In general, the mechanical, chemical, and biological properties of these keratin hydrogels were difficult to control.

Proteinaceous hydrogels, particularly keratin hydrogels, are needed which afford broad control over mechanical, chemical, and biological properties, while maintaining the biocompatibility and healing activity of the proteins.

SUMMARY OF THE INVENTION

The present application provides a network comprising proteinaceous material consisting essentially of water soluble proteins comprising interprotein associations selected from the group consisting of entanglements, electrostatic bonds, covalent bonds consisting essentially of other than disulfide bonds, and combinations thereof.

DETAILED DESCRIPTION OF THE INVENTION

Figure 1:
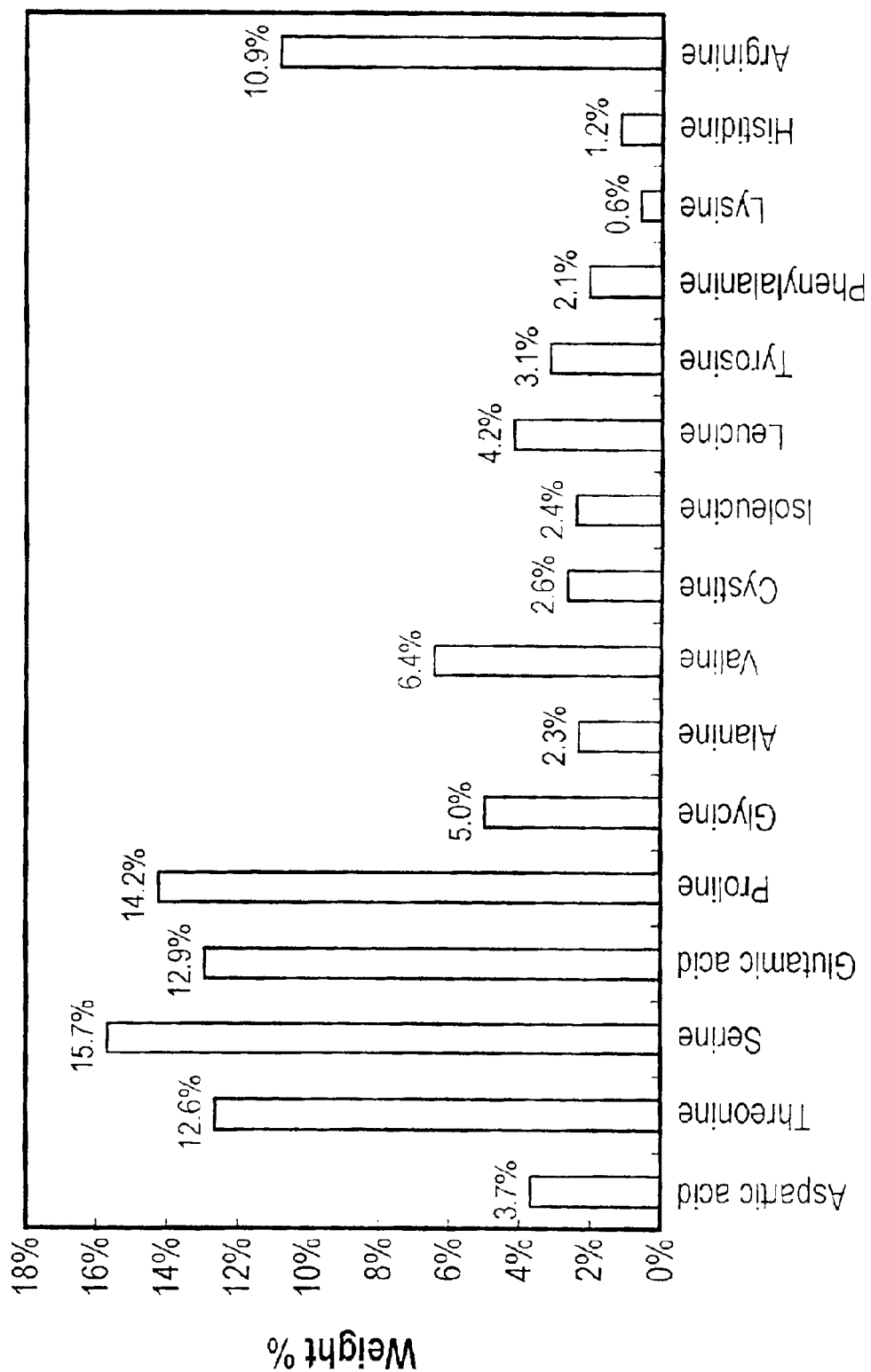
FIG. 1 is an amino acid analysis of reductively extracted low molecular weight keratins, specifically sample 4-AKR-112-2A from Example 3.

The present application provides proteinaceous networks and hydrogels made using the proteinaceous networks. The proteinaceous networks preferably comprise water soluble proteins, preferably water soluble keratins, crosslinked in a manner that affords broad control over mechanical, chemical, and biological properties. The presence of some disulfide crosslinking is not excluded from the networks; however, the crosslinking preferably consists essentially of hydrolyzable and non-hydrolyzable crosslinks to provide control over biodegradability.

A large variety of proteins may be used to form the networks and hydrogels. The proteins preferably have a molecular weight of at least about 10 kDa, preferably at least about 40 kDa, and most preferably about 60 kDa. The proteins are biocompatible, with the result that they inherently provide control over biological compatibility. Examples of suitable naturally occurring proteins include, but are not necessarily limited to proteins derived from keratin, collagen, and elastin. The proteins may be derived from natural, synthetic, or recombinant sources. A preferred source of keratin proteins is hair or fur. The hair may be animal, or human. Preferred proteins are relatively high in cysteine content. Most preferred proteins are keratins, preferably water soluble keratins, even more preferably water soluble α-keratins, most preferably water soluble high molecular weight keratins (HMWK's).

Keratins are loosely defined as the hardened and insolubilized proteins found in the epidermal cells of vertebrates. Human hair is composed almost entirely of keratins. Human hair has a cuticle, which is a tough tubular outer layer made up of flattened cells arranged in a scaly, overlapping profile. The inner bulk of the hair is called the cortex and is constructed from elongated cells that are densely packed with fibrous keratins. The fibrous keratins are arranged in bundles referred to as microfibrils and possess an α-helical tertiary structure. The microfibrils are bound together with an amorphous keratin matrix.

The amorphous keratin matrix and the microfibrils vary in function and composition. The matrix is the "glue" that holds the microfibrils together. This matrix "glue" is high in sulfur content, and is comprised of low molecular weight keratins (LMWK) which typically have an average molecular weight of from about 10 to about 15 kDa. The microfibrils are comprised of α-keratins, including high molecular weight keratins (HMWK), having a relatively lower sulfur content, but having a higher average molecular weight of typically from about 50 to about 85 kDa.

HMWK's and LMWK's vary in chemical properties, such as reactivity and solubility.

Keratins are afforded their structural integrity, in large part, by the presence of disulfide crosslinks which form a three dimensional network of polyprotein chains. This network structure renders keratins insoluble. Keratins can, however, be made water soluble by destroying this three dimensional structure via disulfide bond scission. Disulfide bond scission can be performed either oxidatively, reductively, or using some combination of both types of bond scission. Oxidative bond scission with hydrogen peroxide, for example, results in the formation of sulfonic acid residues produced from cystine. The material produced using hydrogen peroxide for disulfide bond scission is highly ionic and has excellent water solubility. Reductive bond scission with mercaptoethanol, for example, results in the formation of cysteine residues produced from cystine. The material produced using this reductive technique is highly reactive and will readily re-crosslink.

Disulfide Bond Scission and Keratin Extraction

Although the method and hydrogels are not limited to keratins, the following description refers to keratins for the salke of simplicity. The keratins may be processed and/or isolated in a number of ways. Preferably, the processing is sufficient to render the resulting proteins water soluble. Suitable processing techniques include known oxidation techniques, reductive techniques, and/or combinations thereof, as long as the processing renders the proteins water soluble without significant hydrolysis of peptide bonds. At least in the case of keratins, preferred proteins are HMWK's which are processed and isolated by a two step reduction process.

A number of reductive chemistries are known for disulfide bond scission in keratins: See Wardell, J. L., "Preparation of Thiols" in *The Chemistry of the Thiol Group*, Patai, S. (Editor), pp. 163–353, John Wiley & Sons, New York, N.Y. (1974), incorporated herein by reference. HMWK's may be extracted from hair using at least two reductive extractions, as described in Crewther, W. G., Fraser, R. D. B., Lennox, F. G., and Lindley, H., "The Chemistry of Keratins" in *Advances in Protein Chemistry*, Anfinsen, C. B., Jr., Anson, M. L., Edsall, J. T., and Richards, F. M. (Editors), Academic Press, New York, pp. 191–346 (1965), incorporated herein by reference.

In a preferred embodiment, a first reductive extraction is performed by treating the hair with a first reducing agent under first conditions effective to selectively extract matrix keratins, producing a first solution comprising soluble reduced matrix keratins (LMWK's) and remaining hair solids (HMWK's). Although it may be possible to subject the LMWK's to the techniques described herein to produce hydrogels, preferred proteins for use in the techniques herein are HMWK's, which preferably are isolated during a second extraction. The remaining hair solids and the first solution are separated, and the remaining hair solids are exposed to a second extraction solution under second conditions effective to solubilize α-keratins, producing a second solution comprising soluble reduced α-keratins (HMWK's) and solid cuticle.

Suitable reducing agents include, but are not necessarily limited to thioglycolic acid and salts thereof, mercaptoethanol, dithiothreitol, thioglycerol, thiolactic acid, glutathione, cysteine, sodium sulfide, and sodium hydrosulfide. Preferred reducing agents are thioglycolic acid and mercaptoethanol, most preferably thioglycolic acid.

In order to selectively reduce and extract the desired proteins, the hair (or other protein source) is suspended in a reducing agent at a concentration of from about 0.1M to about 10M, preferably about 1.0M. Gentle swelling of hair fibers is achieved at a pH of about 9 or more, preferably at a pH of from about 9 to about 10.5. Hence, the initial reduction takes place at a temperature of from about 20 to about 100° C., preferably at about 25° C. The time period required to accomplish the first reduction is from about 4 to about 24 hours, most preferably about 12 hours. The reaction occurs under an inert atmosphere, preferably nitrogen. The liquid fraction is separated from remaining solids using known means, including but not necessarily limited to filtration, cannulation, and/or centrifugation, preferably under inert atmosphere. A preferred method of separation is filtration.

A second extraction is performed using a suitable swelling agent, preferably urea, bases such as ammonium hydroxide, sodium hydroxide, or potassium hydroxide. A most preferred swelling agent for this second extraction is concentrated urea. The second extraction effectively removes the fibrous α-keratins from inside the cuticle. The second extraction occurs at from about 1M to about 10M urea, preferably about 7M urea, for a period of at least about 1 hour, preferably from about 1 to about 72 hours, most preferably about 24 hours. The second extraction occurs at room temperature, but may take place at temperatures of from about 20° C. to about 100° C., preferably about 25° C. The liquid fraction is separated from the empty, intact cuticle, using known means. Suitable means include but are not necessarily limited to filtration, cannulation and/or centrifugation, preferably under inert atmosphere. A preferred method of separation is filtration.

Once the cuticle is removed, the water soluble keratin proteins may be retained in solution for further use, or they may be isolated from the solution by addition to a water-miscible non-solvent, or by spray drying. Water-miscible non-solvents include, but are not necessarily limited to ethanol, methanol, isopropyl alcohol, tetrahydrofuran, acetone, dioxane, and the like, again under inert atmosphere. A preferred non-solvent is ethanol. The precipitate is separated from the non-solvent using known means, preferably by filtration and rinsing using additional aliquots of the non-solvent. The precipitated proteins are dried using known techniques, preferably overnight under vacuum at room temperature. The extracted water soluble keratin proteins (herein sometimes collectively referred to as "water soluble proteins") comprise thiols or thiol groups.

Thiols possess reactivities similar to alcohols, and can be used to perform a multitude of known organic chemical reactions, such as those described in McMurry, J., *Organic Chemistry*, Brooks/Cole Publishing Co., Monterey, Calif. (1984); Scudder, P. H., Electron Flow in Organic Chemistry, John Wiley & Sons, New York, N.Y. (1992); Stowell, J. C., *Intermediate Organic Chemistry*, John Wiley & Sons, New York, N.Y. (1994), incorporated herein by reference. The rate of reduction is affected by reagent concentration(s), reaction temperature(s), and exposure time(s).

Hydrogels, Generally

Hydrogels are networks of hydrophilic macromolecules that swell in water, but do not dissolve. Hydrogels are used in a variety of medical applications. The network of hydrophilic macromolecules can comprise polymer entanglements (virtual crosslinks), pseudo crosslinks, and/or covalent crosslinks. The point at which the molecular weight of a given macromolecule is sufficient for virtual crosslink formation is known as the critical entanglement molecular weight ($MW_c$). At the $MW_c$, a virtual network is formed, the molecular weight of the material is essentially infinite, and the viscosity increases exponentially as the material reaches its gel point. The macromolecules form pseudo crosslinks when a coordinating molecule attaches itself to two adjacent macromolecules, thus forming a "bond" between them. These types of "bonds" typically are electrostatic in nature, the most common being ionic and hydrogen bonds. Covalent crosslinks typically form the most stable networks.

Regardless of whether the network crosslinks are virtual, pseudo, and/or covalent, the hydrogel resists dissolution because of the nominally infinite molecular weight resulting from the crosslinks. The type of crosslinks found in the network controls the mechanical characteristics of the resulting hydrogel, as well as the in vivo degradation rate as the network is acted upon at the cellular and molecular level.

In order to make a hydrogel using human hair, sufficiently high molecular weight α-keratins from within the microfibrils are selectively extracted and isolated, preferably as described above. Although the exact $MW_c$ for HMWK's is not known, the molecular weight of HMWK's is sufficiently high for virtual crosslink formation and creation of a three-dimensional keratin network. The keratins in the network are hydrophilic in nature. As a result, the three-dimensional keratin network may be swelled with water to produce a hydrogel. Gelation and swelling can be enhanced by the presence of ions. The keratin network is able to sequester the ions, which form pseudo crosslinks and make the network even more hydrophilic.

Unfortunately, hydrogel networks formed solely of critical entanglements and/or pseudo crosslinks may not be sufficiently stable for many uses since the proteins in such hydrogel networks are not covalently linked. In order to produce truly stable hydrogels that exhibit little to no "creep," covalent crosslinks must be introduced into the hydrogel.

The present application describes suitable covalent crosslinks for forming more stable proteinaceous, preferably keratinaceous hydrogels, and provides methods for forming proteinaceous networks comprising such covalent bonding. The hydrogels comprising covalent crosslinks may be engineered to produce a predetermined rate of biodegradation. The rate of biodegradation is controlled by (a) providing hydrolyzable and/or non-hydrolyzable covalent bonding between the proteins in the hydrogel; and (b) manipulating the accessibility of the covalent crosslinks to water molecules.

Covalent bonds that are susceptible to hydrolytic cleavage, such as ester or ether bonds, can be used to impart a relatively rapid biodegradation rate. Conversely, hydrolytically stable bonds such as carbon-carbon, carbon-nitrogen, and carbon-sulfur bonds can be used to extend in vivo biostability. The accessibility of the crosslink to water molecules is manipulated by the introduction of steric hindrance, preferably by flanking susceptible bonds with hydrophobic groups to impart hydrolytic stability.

Formation of Covalent Crosslinks

Thiols and other chemical moieties contained in amino acid residues have utility as labile sites for covalently crosslinking the water soluble proteins. Preferred reactions are reactions that form other than disulfide bonds.

In a preferred embodiment, crosslinking agents are used to produce covalent bonding. Preferred crosslinking agents produce biocompatible byproducts, preferably hydrogen, water, carbon dioxide, and/or any other biocompatible byproduct that is readily metabolized or excreted, removed from the network, or at least is not toxic to the human body.

In order to prepare the networks, the desired crosslinking agent(s) are determined. Crosslinking agents having two or more of the same functional groups, or two or more different functional groups are suitable. Preferable crosslinking agents have two or more of the same functional group, as described below.

In a preferred embodiment, the HMWKs are provided as a dry powdered precursor. The crosslinking agent is provided in an aqueous solution which is added to the powdered HMWKs. Upon mixing, a viscous hydrogel results. The aqueous solution of crosslinker is prepared such that at least about 5 wt. %, preferably about 10 wt. %, relative to the keratin, of the multifunctional crosslinking agent is added, forming a hydrogel. Depending upon the crosslinking agent, a catalyst or promotor may be added. The hydrogel may also be formed first by adding the water to the HMWK powder, followed by adding the crosslinking agent and a catalyst.

Crosslinking Reactions

Crosslinking of the water soluble proteins and network formation occurs, generally, when a non-reactant which is at least difunctional, or has at least two reactive groups, is used to crosslink between reactive pendant groups on two different water soluble keratin proteins. The non-protein reactant creates a bridge between the water soluble proteins, thereby producing a three-dimensional network.

Proteins comprise amino acids, which generally have the formula:

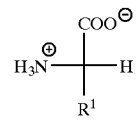

Table 1 summarizes the amino acid residues found in human hair, for example, and shows the "$R^1$" groups associated with each residue.

TABLE 1

Ranked average amounts of amino acids in human hair

| Amino Acid | $R^1$ Group | Nature | pKa | Isoelectric Point (pH) | Percent Composition in Hair |
|---|---|---|---|---|---|
| Cysteine | H—S—CH$_2$— | Nonpolar | 8.4 | 5.02 | 17.3 |
| Glutamic Acid | HO—C(=O)—CH$_2$—CH$_2$— | Polar | 4.5 | 3.22 | 13.9 |
| Arginine | NH$_2$—C(=NH)—N(H)—(CH$_2$)$_3$— | Polar | 12.5 | 11.15 | 9.85 |
| Serine | HO—CH$_2$— | Polar | None | 5.68 | 9 |
| Threonine | CH$_3$—CH(OH)— | Polar | None | 5.64 | 7.75 |

TABLE 1-continued

Ranked average amounts of amino acids in human hair

| Amino Acid | R¹ Group | Nature | pKa | Isoelectric Point (pH) | Percent Composition in Hair |
|---|---|---|---|---|---|
| Leucine | (CH₃)₂CH—CH₂— | Hydrophobic | None | 5.98 | 7.35 |
| Proline | (pyrrolidine ring structure) | Hydrophobic | None | 6.3 | 6.95 |
| Aspartic Acid | HO—C(=O)—CH₂— | Polar | 4.5 | 2.77 | 5.8 |
| Valine | (CH₃)₂CH— | Hydrophobic | None | 5.96 | 5.7 |
| Isoleucine | CH₃—CH₂—CH(CH₃)— | Hydrophobic | None | 5.94 | 4.75 |
| Glycine | H— | Nonpolar | None | 5.65 | 4.15 |
| Phenylalanine | C₆H₅—CH₂— | Hydrophobic | None | 5.48 | 3 |
| Alanine | CH₃— | Hydrophobic | None | 6 | 2.8 |
| Tyrosine | HO—C₆H₄—CH₂— | Hydrophobic | None | 5.66 | 2.6 |
| Lysine | NH₂—(CH₂)₄— | Polar | 10.4 | 9.59 | 2.5 |
| Histidine | (imidazole)—CH₂— | Aromatic | 6.2 | 7.47 | 0.9 |
| Methionine | CH₃—S—CH₂—CH₂— | Hydrophobic | None | 5.74 | 0.85 |
| Tryptophan | (indole)—CH₂— | Hydrophobic | None | 5.89 | 0.85 |

The most abundant amino acid in human hair is cysteine, which is found in the form of disulfide-bridged cystine groups. As discussed above, this group can be converted to other sulfur containing moieties, most notably thiol. Thiols theoretically can be reacted with reactive ends of a crosslinking agent using a number of chemical techniques, such as those described in S. Patai (Ed.), *the Chemistry of the Thiol Group*, Parts 1 and 2, John Wiley & Sons, New York, N.Y. (1974), incorporated herein by reference. Other reaction scenarios, such as those directed toward polymer synthesis, also are useful to utilize thiols to form an assortment of desirable crosslinks, including those described in Rempp, P. and Merrill, E. W., *Polymer Synthesis*, Huethig & Wepf Verlag Basel, Heidelberg, Germany (1986); Young, R. J. and Lovell, P. A., *Introduction to Polymers*, Chapman & Hall, London (1991); Odian, G., *Principles of Polymerization*, John Wiley & Sons, New York, N.Y. (1991), incorporated herein by reference.

In addition to cysteine, the following amino acids have pendant groups comprising nitrogen or oxygen which may be useful as reactive pendant groups; arginine, serine, glutamic acid, threonine, aspartic acid, lysine, asparagine, glutamine, tyrosine, tryptophan, and histidine. Where the protein is α-keratin, preferred amino acid residues comprising reactive pendant groups for crosslinking are cysteine, arginine, serine, and glutamic acid, most preferably cysteine and arginine.

Crosslinking agents comprise at least two reactive groups. Preferred reactive groups are selected from the group consisting of epoxide groups, isocyanate groups, and carboxyl groups. Most preferred crosslinking agents are diepoxides, diisocyanates, and dicarboxylates, including anhydrides and hydrolyzed diacids thereof. For convenience, the crosslinking agents described herein sometimes are referred to as "di-" functional. However, unless a crosslinking agent is expressly claimed or expressly stated to be di-functional only, it is to be understood that the crosslinking agents described herein may also be multi-functional, e.g., di-, tri, tetra-, etc. The non-functional portion of the molecule ($R^5$, below) generally forms the remainder of the "bridge" crosslinking the proteins. $R^5$ is biocompatible and typically is an organic moiety. Suitable organic moieties include, but are not necessarily limited to alkoxy groups, alkylene groups, and alkenyl groups having from about 1 to about 50 carbon atoms. The alkoxy groups, alkylene groups, or alkenyl groups may be present alone, or in combination with cyclic alkyl groups or aromatic groups.

Without limiting the invention to a particular theory or mechanism of action, unless expressly claimed, the following are crosslinking chemistries involved in producing the crosslinked water soluble protein networks:

Conversion of Thiol by Condensation

Condensation reactions such as transesterification, for example, can be used to generate thioesters. An example of a transesterification reaction is shown below:

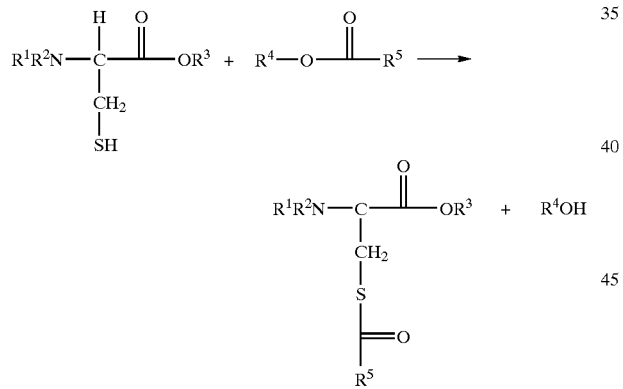

wherein $R^1$ and $R^2$ comprise entities selected from the group consisting of hydrogen and the remainder of the N-terminal portion of the protein molecule; $R^3$ comprises the remainder of the carboxy-terminal portion of the protein molecule; $R^4$ is an appropriate leaving group; and, $R^5$ is a functional hydrocarbon. Suitable $R^4$ groups include, but are not necessarily limited to hydrogen, alkyl groups having from about 1 to 6 carbon atoms, and aryl groups, including benzyl groups. Suitable $R^5$ groups include, but are not necessarily limited to aryl groups, including benzyl groups, and alkyl and allyl groups having from about 1 to about 20 carbon atoms in combination with any number of heteroatoms, such as oxygen and nitrogen, and polyalkylethers comprising from about 1 to 50 repeat groups.

In order to use this reaction to crosslink water soluble keratins a hydrogel comprising from about 1 wt. % to about 20 wt. % water soluble keratins is exposed to a multi-ester or an anhydride of a multi-ester. Suitable multi-esters include, but are not necessarily limited to diesters having from about 1 to 3 carbon atoms (methyl, ethyl, and propyl diesters, respectively) of desired alkyl and aryl carboxylic acids. A preferred embodiment uses phthalic anhydride, which is hydrolyzed to phthalic acid. The exemplary reaction with terephthalic acid is believed to proceed as follows:

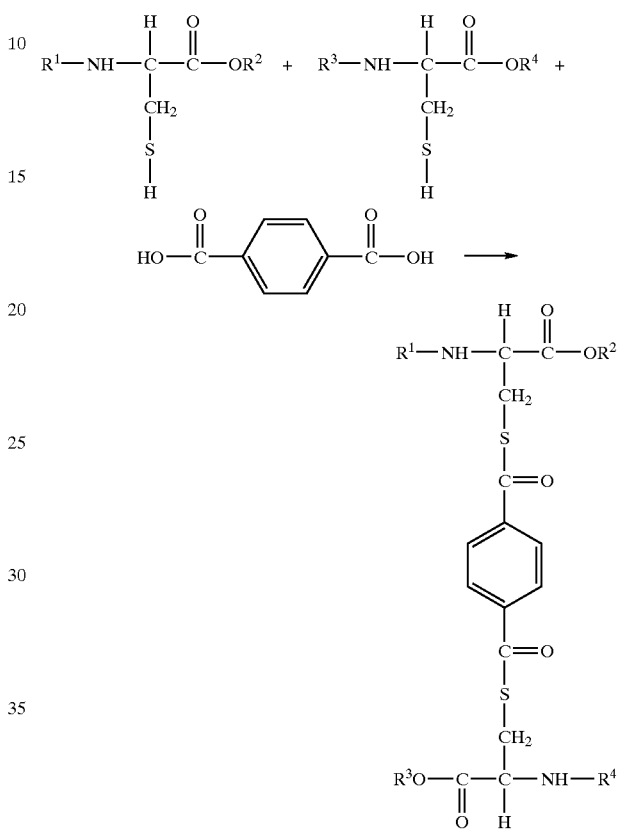

wherein $R^1$ and $R^2$ represent the remainder of a first water soluble protein molecule and $R^3$ and $R^4$ represents the remainder of a second water soluble protein molecule, preferably different α-keratin molecules.

The multi-ester or anhydride typically is at a concentration of up to about 20 weight percent relative to keratin, preferably between 5 and 10 weight percent relative to keratin, most preferably about 10 weight %. The pH is less than about 7, preferably from about 5 to about 7. The temperature is from about 0 to about 100° C., preferably about 60° C. The exposure is continued for a time period of from about 1 hour to about 72 hours, most preferably about 24 hours. Mineral acid catalysts, such as hydrochloric acid, typically can be employed.

Addition to Unsaturated Hydrocarbon

Addition reactions, such as free radical addition to an unsaturated hydrocarbon represents another potential avenue to transformation of the thiol group. A variety of allyl derivatives, for example, can be used to modify the thiol in the presence of an appropriate catalyst or free radical initiator. Many free radical initiators exist that are conveniently activated by heat or light. The free radical addition reaction scenario is shown in the following formula:

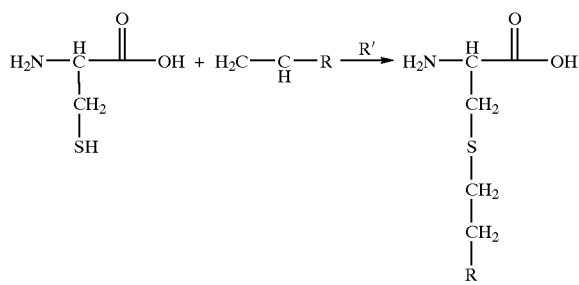

A similar reaction occurs with cysteine, as follows:

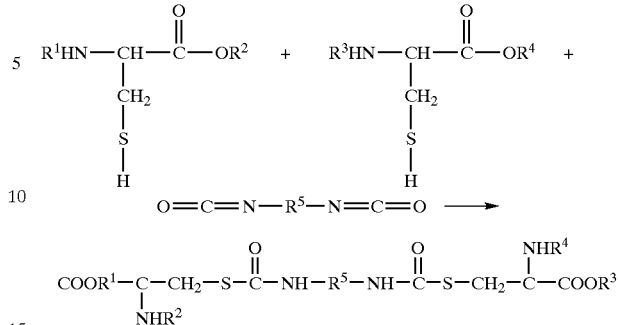

Addition of Isocyanate to Hydroxyl Groups

In another preferred embodiment, a diisocyanate is reacted with hydroxyl groups in the keratin, such as those contained in serine. The reaction is shown below:

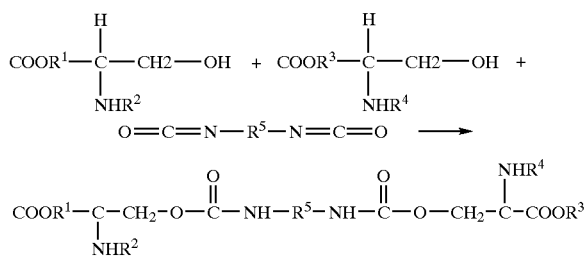

wherein $R^1$ and $R^2$ represent the remainder of one water soluble protein molecule, and $R^3$ and $R^4$ represent the remainder of a second water soluble protein molecule preferably a different α-keratin molecule. $R^5$ may be a variety of organic moieties effective to produce hydrogels having the desired properties. In a preferred embodiment, $R^5$ is selected from the group consisting of aryl groups, including benzyl groups, and alkyl and allyl groups having from about 1 to about 8 carbon atoms, and polyalkylethers containing from about 1 to 50 repeat groups. In a preferred embodiment, $R^5$ is an alkyl group having 6 carbon atoms.

A similar reaction occurs with arginine:

In order to perform these reactions, the crosslinking agent is preferably dissolved in an anhydrous solvent, such as methanol, ethanol, isopropyl alcohol, dimethylsulfoxide, acetone, or tetrahydrofuran. The concentration of this solution is such that the appropriate amount of crosslinking agent is added as the hydrogel is formed. For example, to form a hydrogel with 10 wt. % crosslinking agent and 5 wt. % HMWK solids, 1 gram of a solution containing 0.1 grams of crosslinking agent dissolved in the anhydrous solvent is added to 1.0 gram of HMWK powder dissolved in 18 gm of water. The solution and powder are thoroughly mixed and a hydrogel spontaneously forms. This hydrogel is allowed to react under the time and temperature conditions described previously to effect crosslinking. Crosslinking reactions can be accelerated by incubating this gel in a closed atmosphere at a temperature of from about 25° C. to about 80° C., preferably 37° C.

Addition of Amine Groups

Addition reactions between reactive amine groups and oxirane compounds occur readily without the aid of a catalyst. The crosslinking reaction with arginine is as follows:

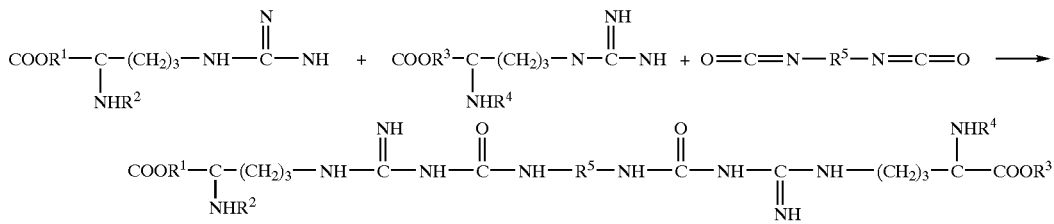

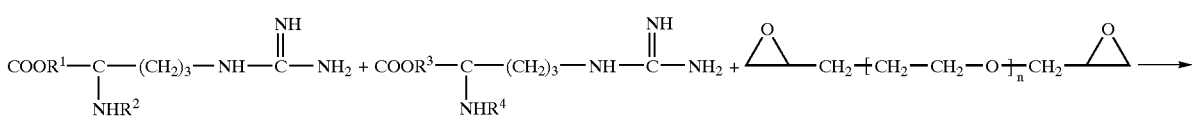

-continued

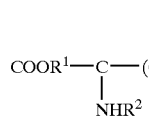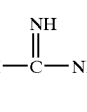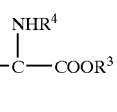

wherein $R^1$ and $R^2$ represent the remainder of one water soluble protein molecule and $R^3$ and $R^4$ represent the remainder of a separate water soluble protein molecule, preferably different water soluble α-keratin molecules.

In order to perform this reaction, the water soluble keratins are exposed to a solution containing an oxirane-containing aliphatic or aromatic compound, typically at a concentration of up to about 20 mole percent relative to keratin, preferably between 5 and 10 mole percent relative to keratin; at a pH between about 4 and 9, preferably about 7; at a temperature of from about 0 to about 100° C., preferably about 37° C., preferably for a time period of from about 0 to about 72 hours, most preferably about 24 hours. This process results in the formation of a hydrogel within 1 to 2 minutes and the crosslinking reaction occurs while the keratins are in the gelled state.

A preferred oxirane compound is a diepoxide having the following general structure:

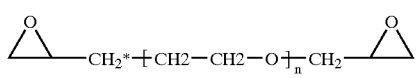

wherein n is from about 1 to about 50. Preferred epoxides include DER™ 332 and DER™ 736, available from the Dow Chemical Company.

A similar reaction occurs when a diepoxide reacts with cysteine residues:

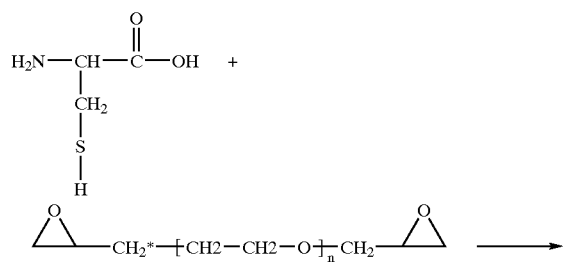

-continued

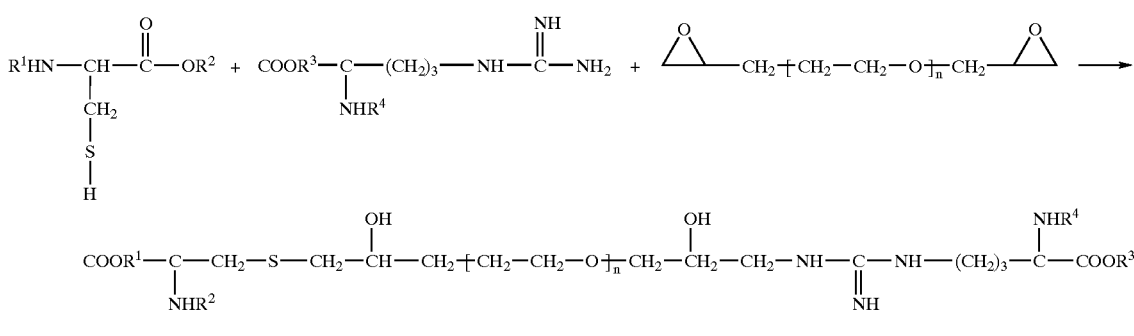

wherein $R^1$ and $R^2$ are the remainder of a first water soluble protein molecule and $R^3$ and $R^4$ are the remainder of a second water soluble protein molecule.

Persons of ordinary skill in the art will recognize that many of the crosslinking agents described herein will react with a variety of amino acid residues having pendant groups comprising a reactive nitrogen atom, sulfur atom, or oxygen atom. Hence, one end of a diepoxide may react with a cysteine residue while the other end of the diepoxide reacts with an arginine residue, as follows:

The identity of amino acid residues linked by the crosslinking agent is not as important as the requirement that a sufficient quantity of crosslinking between water soluble proteins occurs to produce a network and preferably a hydrogel having desired properties.

Network Properties

As seen below, a three dimensional water soluble protein-based network can be formed using a variety of chemistries. Preferably, the "dissolution rate" of such a network is controllable by controlling the crosslink density of the network and the level and type of functionality, particularly the functionality adjacent to the crosslink site. For example, the use of a crosslinking agent having one of the following characteristics reduces the dissolution rate of the resulting network: a crosslinking agent which forms S—C bonds, as opposed to more hydrolyzable bonds, such as ester bonds; a crosslinking agent which introduces substantial steric hindrance at the crosslink site; a crosslinking agent which is hydrophobic. The "dissolution rate" of the resulting network or hydrogel is measured by determining how long the network resists hydrolysis upon exposure to an aqueous buffer having a pH of about 7. A desirable "dissolution rate" will depend upon the application in which the hydrogel is to be used.

The invention will be better understood with reference to the following Examples, which are illustrative only:

EXAMPLE 1

800 mL of 0.8M thioglycolic acid (TGA) at pH 10.2, adjusted by addition of 52.58 grams of potassium hydroxide (KOH), was added to a 1 L glass reactor containing 40 grams of human hair obtained from a local barber shop. The hair had been washed with an aqueous solution of mild detergent, rinsed, and air dried prior to use. The mixture was stirred gently at room temperature (ca. 25° C.) under positive nitrogen pressure for 18 hours.

The reaction mixture was filtered and the extract titrated to pH 7 by addition of hydrochloric acid (HCl). The neutralized solution was added dropwise to a 10-fold excess of absolute ethanol, while stirring, to promote the formation of a precipitate. The precipitate was filtered and dried under vacuum.

The remaining reduced hair was further processed by first rinsing it free of residual reductant using copious amounts of deionized water, upon which the hair swelled to nearly twice its initial volume. The rinsed hair was placed in a 2 L reactor to which was added 400 mL of 7M urea solution. The reaction was stirred at room temperature under positive nitrogen pressure for 24 hours.

100 mL of the reaction mixture was centrifuged and filtered. The pH of the filtered extract was titrated to pH 7 with the addition of HCl. The neutralized solution was added dropwise to 900 mL of absolute ethanol to affect precipitation. The solid keratins were isolated by filtration and hydrated with 18 MΩ water, upon which, a thick hydrogel formed.

EXAMPLE 2

800 mL of 1M mercaptoethanol at pH 10.2, adjusted by addition of ca. 24 grams of KOH, was added to a 1 L glass reactor containing 40 grams of human hair obtained from a local barber shop. The hair had been washed with an aqueous solution of mild detergent, rinsed, and air dried prior to use. The mixture was stirred gently at room temperature under positive nitrogen pressure for 18 hours. After extraction, the mixture was filtered and the liquid discarded.

The remaining reduced hair was further processed by first rinsing it free of residual reductant using copious amounts of deionized water, upon which, the hair swelled to nearly twice its initial volume. The rinsed hair was placed in a 2 L reactor to which was added 400 mL of 7M urea solution. The reaction was stirred at room temperature under positive nitrogen pressure for 24 hours.

The reaction mixture was centrifuged and filtered. The pH of the filtered extract was titrated to 7 with the addition of HCl. The neutralized solution was added dropwise to 4,500 mL of absolute ethanol to affect precipitation. The solid keratins were isolated by filtration and dried overnight under vacuum. The dried keratin powder was ground to a medium consistency with a mortar and pestle.

1.0 grams of a 0.01M sodium hydroxide (NaOH) solution was added to a vial containing 0.1 grams of the keratin powder from Example 2, upon which, the mixture formed a thick hydrogel. Another 2.0 grams of 0.01M sodium hydroxide solution was added (3.0 grams total) which reduced the viscosity of the hydrogel only slightly. This process was repeated with 0.001M and 0.0001M NaOH solutions with similar results.

0.5 grams of a 30% ammonium hydroxide ($NH_4OH$) solution was added to a vial containing 0.1 grams of the sample from Example 2, upon which, the mixture formed a thick hydrogel. Subsequent additions of 0.5, 1.0, and 0.5 grams of $NH_4OH$ did not appear to reduce the viscosity of the gel. Addition of a final 0.5 grams of $NH_4OH$ (3.0 grams total) reduced the viscosity only slightly.

EXAMPLE 3

800 mL of 1M mercaptoethanol at pH 10.2, adjusted by addition of ca. 25 grams of KOH, was added to a 1 L glass reactor containing 40 grams of human hair obtained from a local barber shop. The hair had been washed with an aqueous solution of mild detergent, rinsed, and air dried prior to use. The mixture was stirred gently at room temperature under positive nitrogen pressure for 18 hours.

The reaction mixture was filtered and the extract titrated to pH 7 by addition of HCl. The neutralized solution was added dropwise to a 10-fold excess of absolute ethanol while stirring to promote the formation of a precipitate. The precipitate was filtered and dried under vacuum. Yield of keratin solids was 13.37 grams (33.4%). An amino acid analysis of this sample was conducted by acid hydrolysis and dissolution of the solid, followed by high pressure liquid chromatography (HPLC) of the solution. For cysteine residues, an analysis was performed on a separate sample by first oxidizing the solid keratins with performic acid, followed by acid digestion and HPLC analysis. The results of these analyses are summarized in the graph in FIG. 1.

The remaining reduced hair was further processed by first rinsing it of residual reductant using copious amounts of deionized water, upon which, the hair swelled to nearly twice its initial volume. The rinsed hair was placed in a 1 L reactor to which was added 400 mL of 7M urea solution. The reaction was stirred at room temperature under positive nitrogen pressure for 24 hours.

The reaction mixture was centrifuged and filtered. The pH of the filtered extract was titrated to 7 with the addition of HCl. The neutralized solution was added dropwise to 4,000 mL of absolute ethanol to affect precipitation. The solid keratins were isolated by filtration and dried overnight under vacuum. The dried keratin powder was ground to a medium consistency with a mortar and pestle. The yield of keratin solids was 1.66 grams (sample no. 4-AKR-112-2B; 4%).

Three sets of duplicate hydrogels containing 0.1 gram each of the keratin solids and 1.0, 2.0, and 3.0 grams of 30% $NH_4OH$ solution were prepared in glass vials. The weight percent solids in each of these duplicate gels were 9.1, 4.8, and 3.2, respectively. The headspace of one of each of the duplicates was filled with pH 7.2 phosphate buffered saline and the vial capped and sealed with tape. These samples, as well as the set containing no buffer solution (also capped and sealed with tape) were placed in an incubator held at 37° C. (body temperature) and monitored periodically by visual observation.

After 4 days in the incubator, the 2.0-gram gel in saline appear to begin disintegrating into the aqueous layer. There were no visible signs of any changes in the other hydrogels. After 16 days, all of the gels appeared intact, however, the buffer solutions displayed a slight brown discoloration. After 21 days, the gels were removed from the incubator. Other than a slight discoloration of the buffer solution, and a small amount of volume shrinkage in the buffered samples, no changes in any of the hydrogels appeared to have occurred.

EXAMPLE 4

1.0 grams of a 30% ammonium hydroxide ($NH_4OH$) solution was added to a vial containing 0.1 grams of human hair from Example 3. The mixture formed a thick hydrogel.

Figure 2:
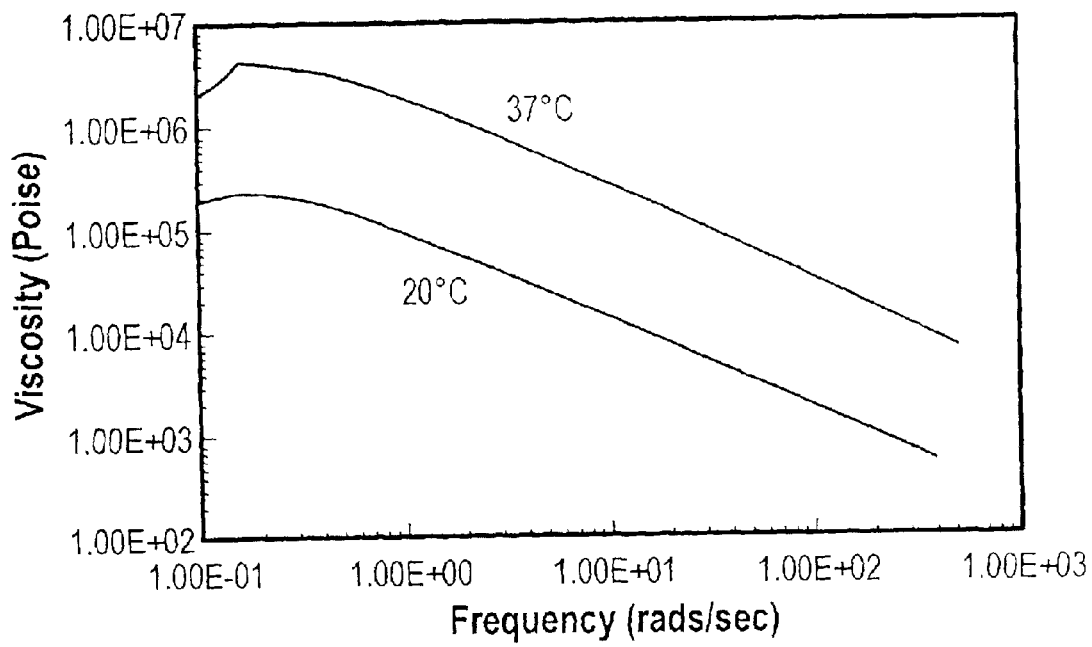
FIG. 2 is a cone and plate viscosity analysis of keratin hydrogel made with 10 weight percent of sample no. 4-AKR-112-2B from Example 5.
Figure 3:
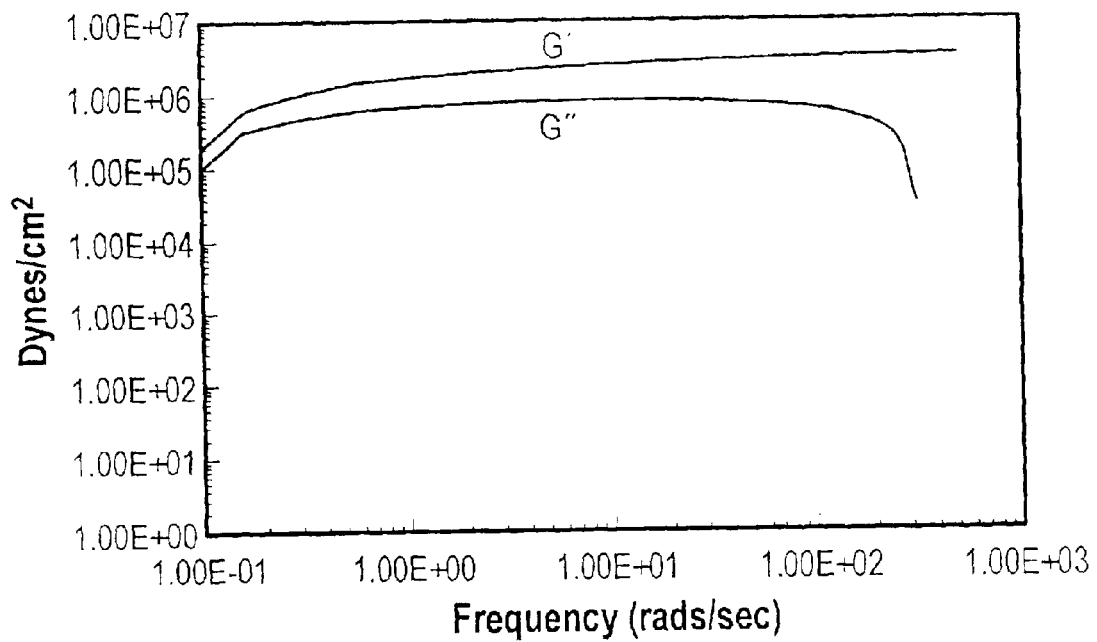
FIG. 3 is a graph of the storage (G') and loss (G") dynamic shear moduli of a keratin hydrogel made with 10 weight percent of sample no. 4-AKR-112-2B from Example 5.

The viscosity of this gel was analyzed using a cone and plate rheometer. The results, shown in FIGS. 2 and 3 suggest that the hydrogel is a classical non-Newtonian fluid.

In a "Newtonian fluid," the coefficient of viscosity at a given temperature and pressure is a constant for that fluid and independent of the rate of shear or velocity gradient. Non-Newtonian fluids consist of two or more phases present at the same time, and the coefficient of viscosity is not constant, but is a function of the rate at which the fluid is sheared as well as of the relative concentration of the phases. Non-Newtonian fluids frequently exhibit plastic flow, in which the flowing behavior of the material occurs after applied stress reaches a critical value or yield point (YP).

The fact that the hydrogel formed was a non-Newtonian fluid served to indicate that the bonding, such as pseudo-bonding or polymer entanglements had occurred within the gel.

EXAMPLE 5

3,500 mL of 1.0M thioglycolic acid (TGA) at pH 10.2, adjusted by addition of 312.5 grams of potassium hydroxide (KOH), was added to a 4 L glass reactor containing 175 grams of human hair obtained from a local barber shop. The hair had been washed with an aqueous solution of mild detergent, rinsed, and air dried prior to use. The mixture was stirred gently at room temperature (ca. 25° C.) under positive nitrogen pressure for 18 hours.

The reaction mixture was sieved and the reduced hair was further processed by first rinsing it free of residual reductant using copious amounts of deionized water, upon which the hair swelled to nearly twice its initial volume. The rinsed hair was placed into two separate glass reactors to which was added 7M urea solution. These extractions were stirred at room temperature under positive nitrogen pressure for 24 hours.

The extracted hair was removed from solution by passing through a sieve. The liquid fraction was centrifuged and filter, then neutralized to pH 7 with the addition of HCl (3.7 mL). The liquid was added dropwise to a 10-fold excess of ethanol to effect precipitation of the HMWKs. The precipitate was isolated by filtration, washed with several aliquots of fresh ethanol, then dried overnight under vacuum. The resulting solid HMWKs were ground to a fine powder using a mortar and pestle.

Figure 4:
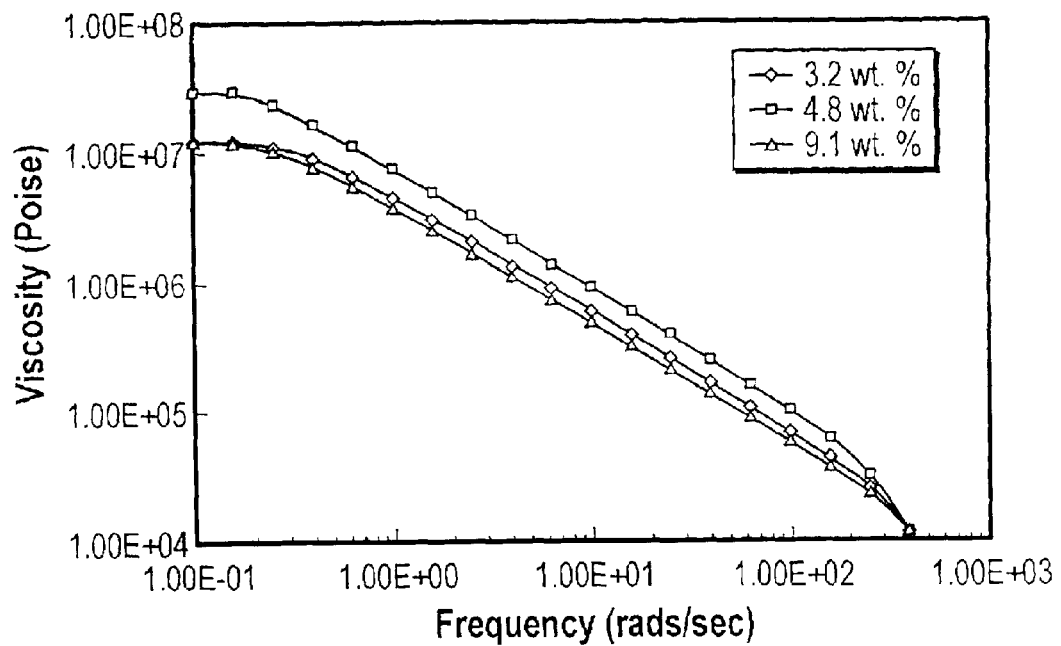
FIG. 4 is a graph of the dynamic shear viscosity of non-crosslinked keratin hydrogels from Example 5.

Nine-100 milligram samples of the powder were placed in glass vials. To each set of three vials was added 1.0, 2.0, and 3.0 grams of deionized water, respectively. The contents of each vial were mixed and allowed to gel. The resulting triplicate set of hydrogels contained 9.1, 4.8, and 3.2 weight % keratins, respectively. To one of each triplicate hydrogel was added enough pH 7.2 phosphate buffered saline solution to fill the headspace of the vial. These samples, as well as identical samples not containing buffer solution, were placed in an incubator held at a constant temperature of 37° C. The third sample of each triplicate was incubated at 37° C. for 24 hours, then analyzed using a cone and plate rheometer. The rheometer was used to determine the shear dependant viscosity at 37° C. of these "un-crosslinked" hydrogels. As used herein, "un-crosslinked" describes hydrogels that have not been reacted with a multifunctional crosslinker per se; such hydrogels will have virtual and pseudo crosslinks present. FIG. 4 shows the results for the 9.1, 4.8, and 3.2 wt. % hydrogels.

Similarly, nine-100 milligram samples of the powder were placed in glass vials. To triplicate samples was added 1.0, 2.0, and 3.0 grams of solutions containing 1.0, 0.5, and 0.33 wt. % of the crosslinker, DER 332 resin, respectively. This was done in order to deliver 0.01 grams (10 wt. % relative to keratin) of dissolved crosslinker to each vial of keratin powder.

Figure 5:
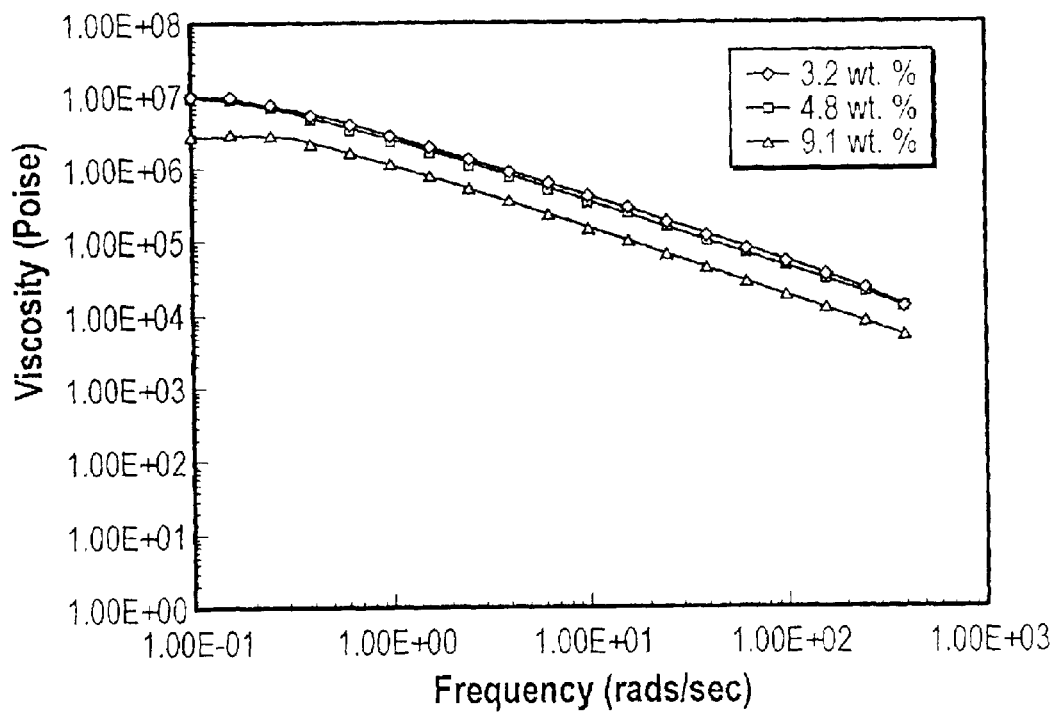
FIG. 5 is a graph of the dynamic shear viscosity of DER 332 resin crosslinked keratin hydrogels of Example 5.

To one of each triplicate hydrogel was added enough pH 7.2 phosphate buffered saline solution to fill the headspace of the vial. These samples, as well as identical samples not containing buffer solution, were placed in an incubator held at a constant temperature of 37° C. The third sample of each triplicate was incubated at 37° C. for 24 hours, then analyzed using a cone and plate rheometer. The rheometer was used to determine the shear dependant viscosity at 37° C. of these crosslinked hydrogels. FIG. 5 show the results for the 9.1, 4.8, and 3.2 wt. % hydrogels containing DER 332 resin crosslinks.

Figure 6:
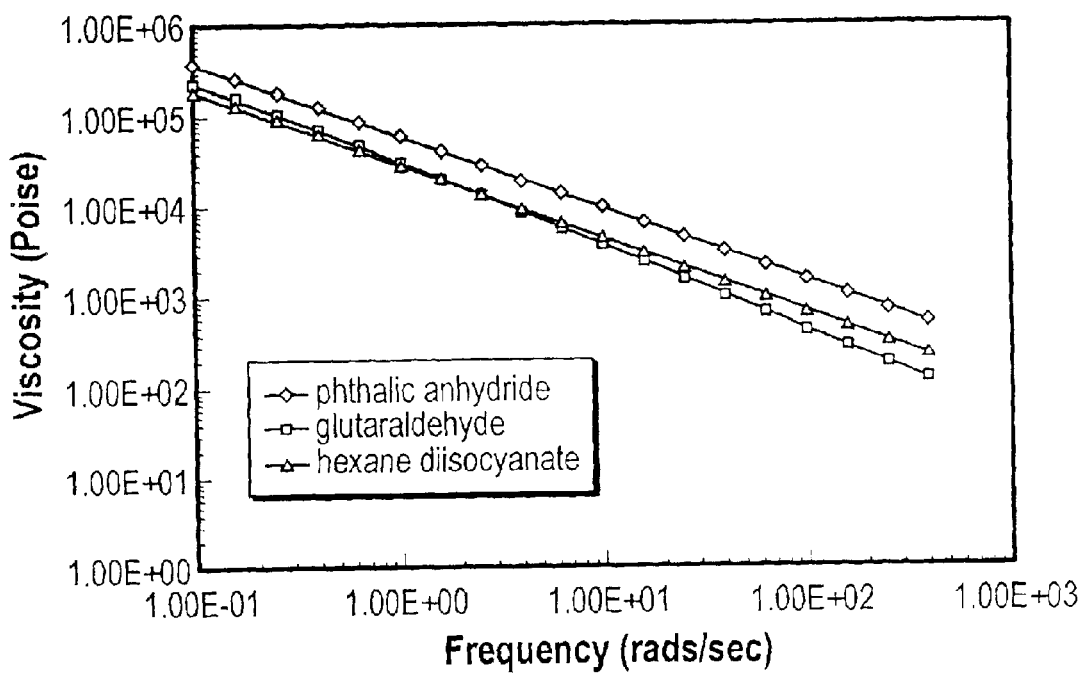
FIG. 6 is a graph of the dynamic shear viscosity of three crosslinked keratin hydrogels of Example 5.

This process was repeated using phthalic anhydride and glutaraldehyde as crosslinkers. Hexane diisocyanate was also used as a crosslinker, but was added directly to the hydrogel as it was forming. The viscosities of the 4.8 wt. % hydrogels for each of these crosslinked systems are shown FIG. 6.

Figure 7:
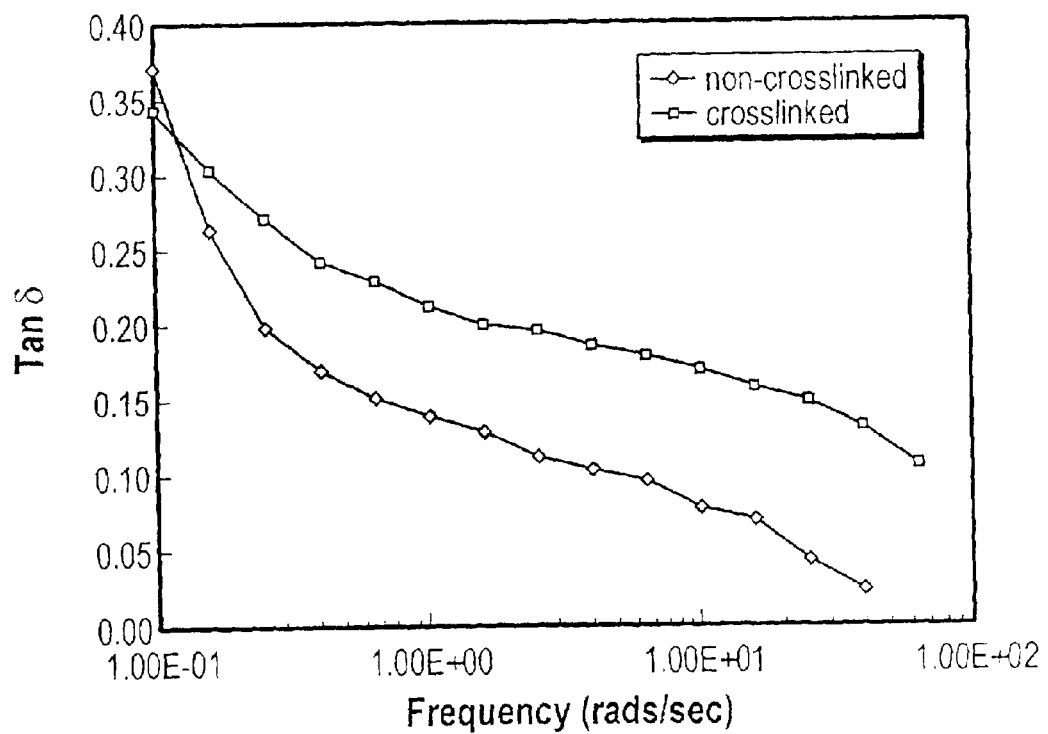
FIG. 7 is a graph of the tan d measurement of non-crosslinked and DER 332 resin crosslinked keratin hydrogels of Example 5.

The impact of the crosslinking reaction was evaluated by comparison of the tan δ (ratio of the shear loss modulus to the shear storage modulus) for two of the gels, the un-crosslinked and the DER 332 resin-crosslinked gels. An overlay of tan δ for the 4.8 wt. % gels are shown in FIG. 7. The flattening tan δ curve of the DER 332 resin-crosslinked hydrogel suggests that this gel is more rigid than the uncrosslinked hydrogel.

The hydrogels subjected to contact with buffer solution at body temperature were checked periodically for degradation via viscosity measurements and UV-Vis spectroscopy of the buffer layer. After more than 6 weeks, no signs of degradation were present in any of the hydrogels.

Persons of ordinary skill in the art will recognize that many modifications may be made to the present invention without departing from the spirit and scope of the present invention. The embodiment described herein is meant to be illustrative only and should not be taken as limiting the invention, which is defined in the claims.

I claim:

1. A composition comprising water soluble keratin proteins of about 40–60 kDa molecular weight, wherein the keratin proteins are substantially free of ultra-protein or inter-protein cystine disulfide bonds, wherein the composition forms a hydrogel when placed in an aqueous ion containing solution, and further wherein the keratin proteins are isolated under reductive conditions and are substantially free of oxidized cystines.

2. The composition of claim 1, wherein the ion containing solution is a solution of sodium hydroxide or ammonium hydroxide.

3. A composition comprising water soluble keratin proteins of about 40–60 kDa molecular weight, wherein the keratin proteins are substantially free of intra-protein or inter-protein cystine disulfide bonds, and wherein at least a portion of the cysteine side chains comprises a disulfide bond, wherein the composition forms a hydrogel when placed in aqueous solution containing monovalent ions.

4. The composition of claim 3 wherein a portion of the cystine side chains comprise a disulfide bond to thioglycolate.

5. The composition of claim 3 wherein a portion of the cystine side chains comprise a disulfide bond to mercaptoethanol.

* * * * *

UNITED STATES PATENT AND TRADEMARK OFFICE
CERTIFICATE OF CORRECTION

PATENT NO. : 7,001,987 B2 Page 1 of 1
DATED : February 21, 2006
INVENTOR(S) : Mark E. Van Dyke It is certified that error appears in the above-identified patent and that said Letters Patent is hereby corrected as shown below:

Column 18,
Line 44, delete "ultra-protein" and insert -- intra-protein --.

Signed and Sealed this

Ninth Day of May, 2006

JON W. DUDAS
*Director of the United States Patent and Trademark Office*